United States Patent
Maini et al.

(10) Patent No.: US 6,976,952 B1
(45) Date of Patent: Dec. 20, 2005

(54) EXPANDED POLYTETRAFLUOROETHYLENE VASCULAR GRAFT WITH COATING

(75) Inventors: Roshan Maini, Bridge of Weir (GB); Karen Kelso, Kilmarnock (GB)

(73) Assignee: Vascutek Limited, Renfrewshire (GB)

(*) Notice: Subject to any disclaimer, the term of this patent is extended or adjusted under 35 U.S.C. 154(b) by 0 days.

(21) Appl. No.: 09/958,999

(22) PCT Filed: Apr. 25, 2000

(86) PCT No.: PCT/GB00/01603

§ 371 (c)(1),
(2), (4) Date: Oct. 15, 2001

(87) PCT Pub. No.: WO01/80918

PCT Pub. Date: Nov. 1, 2001

Related U.S. Application Data

(63) Continuation-in-part of application No. 09/298,296, filed on Apr. 23, 1999, now Pat. No. 6,368,347.

(51) Int. Cl.[7] .............................. A61F 2/04; A61F 2/06
(52) U.S. Cl. .................. 600/36; 623/1.47; 623/1.39
(58) Field of Search ............... 623/921, 1.39, 623/1.4, 1.41–1.48; 600/36; 427/225

(56) References Cited

U.S. PATENT DOCUMENTS

| | | | |
|---|---|---|---|
| 3,272,204 A | 9/1966 | Artandi et al. | 128/334 |
| 4,193,138 A | 3/1980 | Okita | 3/1.4 |
| 4,747,848 A | 5/1988 | Maini | 623/1 |
| 4,842,575 A | 6/1989 | Hoffman, Jr. et al. | 600/36 |
| 5,098,779 A | 3/1992 | Kranzler | 428/306.6 |
| 5,197,977 A | 3/1993 | Hoffman, Jr. et al. | 623/1 |
| 5,665,114 A | 9/1997 | Weadock et al. | 623/1 |
| 5,716,660 A * | 2/1998 | Weadock et al. | 427/2.25 |
| 5,851,229 A * | 12/1998 | Lentz et al. | 623/23.72 |

FOREIGN PATENT DOCUMENTS

EP 0 742 020 A2 11/1996

* cited by examiner

*Primary Examiner*—David H. Willse
*Assistant Examiner*—Hieu Phan
(74) *Attorney, Agent, or Firm*—Drinker Biddle & Reath LLP

(57) ABSTRACT

A vascular graft comprised of a tubular polytetrafluoroethylene (ePTFE) sheet is provided. The ePTFE sheet has a substantially uniform coating of bioresorbable gel material, for example gelatin, on a surface thereof. The coating minimises bleeding through suture holes in the ePTFE sheet and provides an increase in longitudinal extensibility.

12 Claims, 7 Drawing Sheets

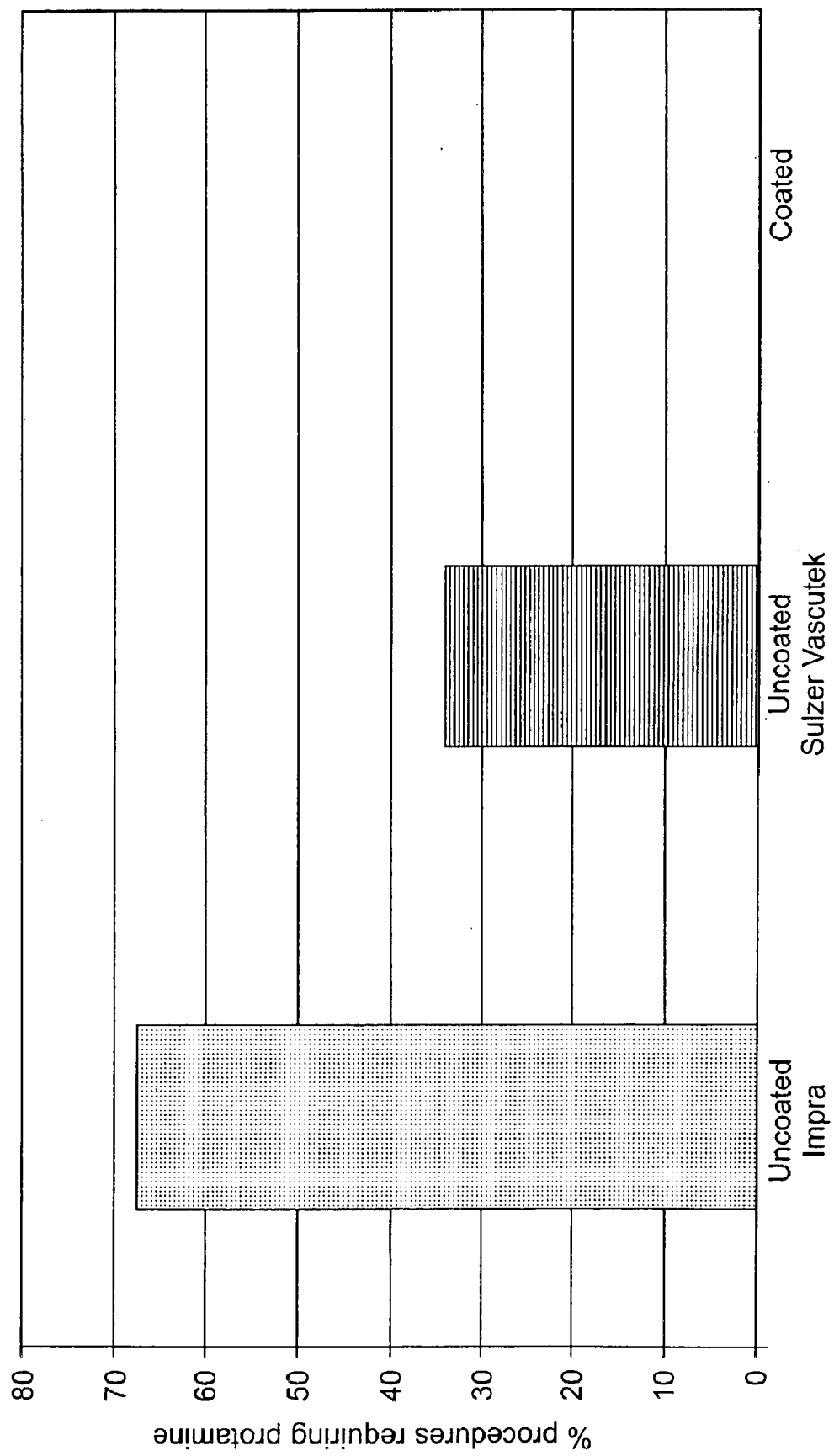

EXPANDED POLYTETRAFLUOROETHYLENE VASCULAR GRAFT WITH COATING

CROSS REFERENCE TO RELATED APPLICATIONS

The present application is a '371 of PCT/GB00/01603, filed on Apr. 25, 2004, which is a continuation in part of the patent application having U.S. Ser. No. 09/298,296, filed on 23 Apr. 1999, now U.S. Pat. No. 6,368,347.

BACKGROUND OF THE INVENTION

1. Field of the Invention

This invention relates to vascular prostheses of polytetrafluoroethylene.

2. Description of Related Art

Vascular prostheses made of knitted or woven fabric of a polyester (e.g. DACRON polyester, a trademark of E.I. du Pont de Nemours & Co., Inc.) or of sheets of polytetrafluoroethylene are currently available, or have been described in the art. Expanded polytetrafluoroethylene (ePTFE) tubes have a microporous structure consisting of small nodes interconnected with many tiny fibrilla. The ePTFE is extruded into tubes to make vascular grafts. Although vascular grafts constructed using such material are generally clinically successful, there is a tendency for the graft to leak blood at suture holes where the graft is attached to a patient. The generally non-resilient characteristics of ePTFE material means that as the suture needles create a hole in the sheet the material cannot conform closely to the smaller diameter of the suture. There is thus a tendency for the graft for blood to leak around the edges of the sutures. Intraoperative measures, including compression or other physical intervention, may need to be taken to reduce or eliminate bleeding and these procedures inevitably prolong operation times and are clearly undesirable.

Previous solutions to the problem of suture hole leakage have relied on filling the porous structure of the ePTFE material with a bioresorbable sealant. For example, Okita, in U.S. Pat. No. 4,193,138, proposed introducing a water-soluble polymer into the pores of the ePTFE material and then treating the polymer to render it water-insoluble. Weadock et al., in U.S. Pat. 5,665,114, proposed filling the pores with solid biocompatible material of natural origin. A water-soluble substance is introduced into the pores and treated to render it water-insoluble.

In connection with grafts made with knitted or woven fabrics, materials such as collagen or gelatin have been applied to the highly porous surface of such textiles. See, for example, U.S. Pat. Nos. 3,272,204; 4,747,848; 4,842,575 or 5,197,977. The materials can be expected to penetrate into the voids produced by the woven or knitted structure of the fabric and thus reduce blood leakage throughout the entire fabric, as well as at locations where sutures pass through the fabric. Of course, since fibres of the fabric will spread apart to allow passage of the suture needle and then return to a closer configuration adjacent a suture, the problem of suture hole leakage in fabric grafts is not as severe as in ePTFE grafts.

BRIEF SUMMARY OF THE INVENTION

The prosthesis of the present invention seeks to overcome the limitations of the prior art by providing an ePTFE vascular graft having a substantially uniform coating of bioresorbable gel on an outer surface thereof. The method of application preferably causes the coating to be confined substantially entirely to the outer surface, meaning that there is minimal penetration of the coating into the pores of the ePTFE material. Preferably, the bioresorbable gel is plasticised with glycerol. Sorbitol might also be used.

BRIEF DESCRIPTION OF SEVERAL VIEWS OF THE DRAWINGS

Preferred embodiments of the invention are described below with reference to the Figures in which:

FIG. 10 is a graph showing the percentage of surgical procedures in Example 5 involving different ePTFE grafts requiring protamine sulfate administration to control blood loss.

DETAILED DESCRIPTION OF THE INVENTION

In the Figures and in this description, like numerals will be used to refer to like parts.

Figure 1:
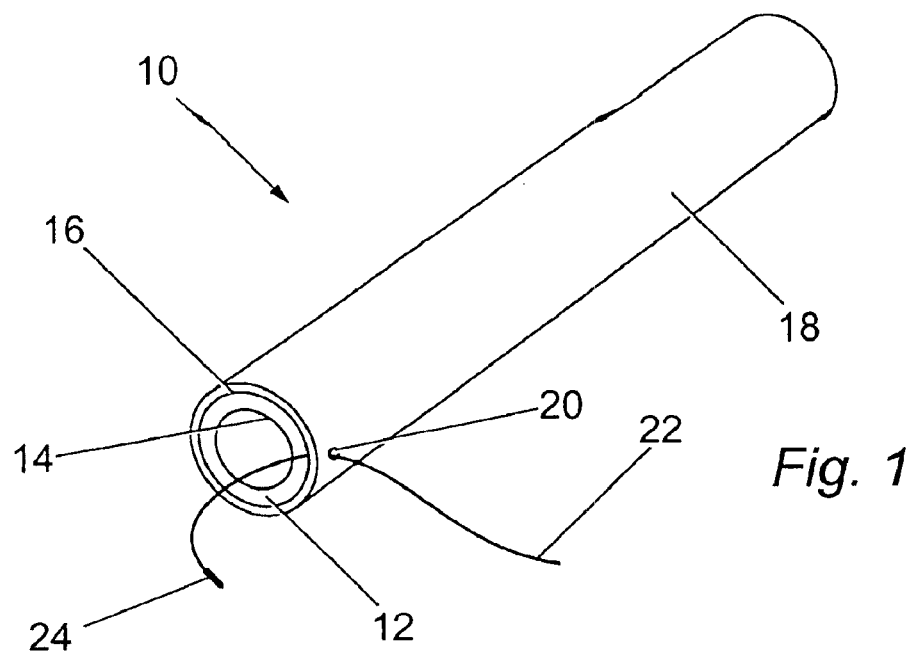
FIG. 1 is a perspective view of a tubular vascular prosthesis.

FIG. 1 illustrates a tubular vascular graft 10. The vascular graft 10 is comprised of a tube of ePTFE material 12 having an inside surface 14 and an outside surface 16. The inside surface 14 is expected to be adjacent a flow of blood when the graft is implanted in the body of a patient. The outside surface 16 is covered with a gel coating 18 (for clarity the thickness of the gel coating has been exaggerated in the Figure). Preferably, the coating 18 in confined to the surface only, and does not penetrate significantly into voids in the ePTFE material. Some slight penetration (usually only a few microns) will occur (see FIG. 6).

Generally, the penetration of the coating into the ePTFE is less than 50 μm, usually less than 20 μm, preferably less than 10 μm, more preferably less than 5 μm.

The thickness of the ePTFE material itself is generally 200–600 μm thick (depending on the graft type), typically 400–500 μm, so that the degree of penetration of the coating into the ePTFE material will generally be less than 10% of the (uncoated) wall thickness, more usually less than 5% and preferably less than 3% (for example 1% or 2%).

Figure 2:
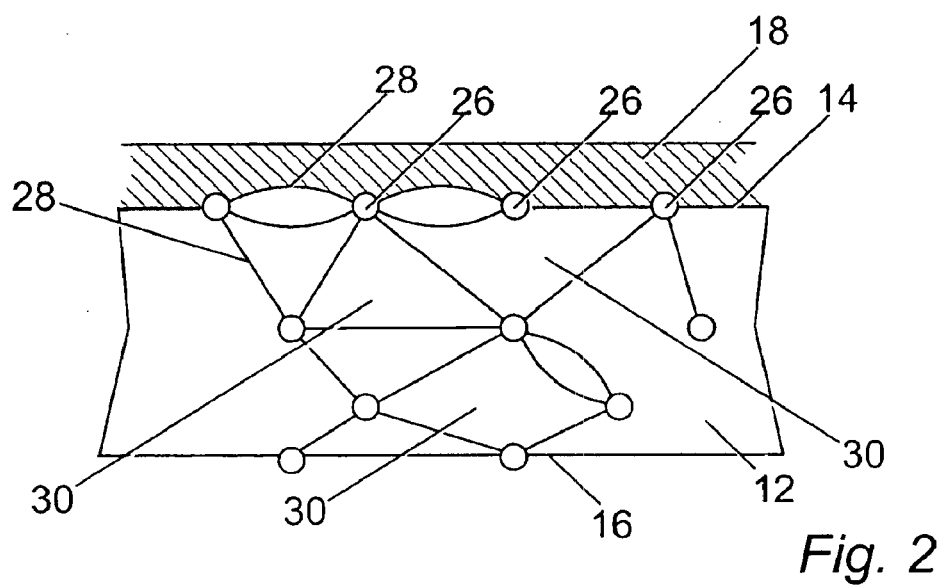
FIG. 2 is a cross-sectional view of a layer of ePTFE material with a gelatin coating.

As illustrated in FIG. 2, the ePTFE material 12 is comprised of a plurality of nodes 26, interconnected by fibrils 28. This structure forms voids or pores 30 between the fibrils.

Those skilled in the art recognise that the character of the fibrils and voids can be modified by various treatments. Whatever the selected size of voids, however, the gel coating 18 remains essentially entirely on the outer surface 14 of the sheet 12. It is thought that this structure enhances the flexibility of the graft 10, while providing sealing around sutures.

Figure 3:
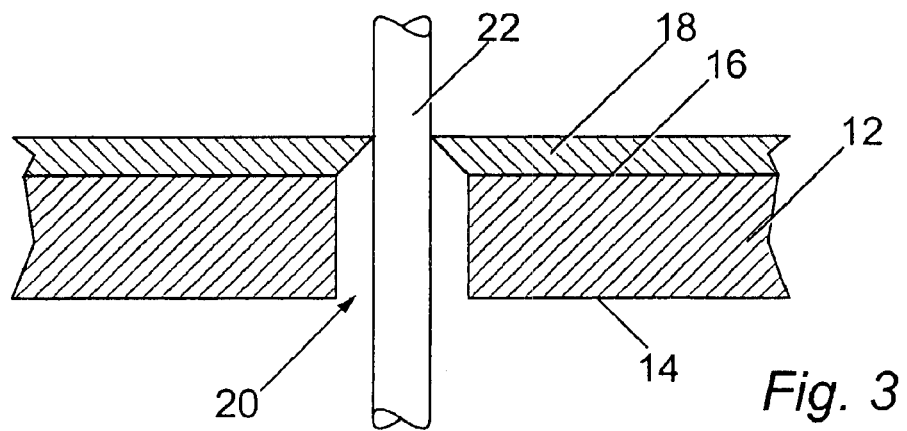
FIG. 3 is a cross-sectional view of the ePTFE material of FIG. 2, illustrating a suture passing through a hole created by a suture needle.

In use, it is contemplated that the graft 10 will be sutured in place within the body of a patient. A suture needle 24 having an attached suture 22 is passed through the ePTFE material 12 and the gel coating 18, producing a suture hole 20. As can be seen in FIG. 3, the needle produces a hole 20 which is wider than the suture 22. Due to the properties of the ePTFE material 12, the material 12 does not collapse elastically around the suture. This can lead to leakage of blood around the suture. In the present invention, however, the gel coating 18 collapses radially around the suture, and closes the suture hole while healing takes place.

The gel coating 18 is preferably a bioresorbable gelatin and any pharmaceutical grade gelatin can be used. A suitable gelatin is a mammalian gelatin, for example as described in U.S. Pat. No. 4,747,848, which is incorporated herein by reference. Such gelatin comprises a mixture of 50% normal limed bone gelatin and 50% normal gelatin treated with chloride of succinic acid. A solution of gelatin in pharmaceutical grade water is convenient for coating the grafts.

Other gels may also be used such as a polysaccharide gel such as Dextran™ gel.

Alternatively, other appropriate synthetic and biological hydrogels may be used. The preparations of such hydrogels are known in the art. Synthetic hydrogels may include poly(2-hydroxyethyl methacrylate) [PHEMA]; poly(vinyl alcohol)[PVA]; poly(ethylene oxide) [PEO]; poly (carboxylic acids); poly(N-vinyl 2-pyrollidene)[PVP] or other synthetic hydrophilic polymers. Biological hydrogels may include starches alginates, celluloses, agars, chitosan, collagen gels and the like.

The gel coating 18 may be applied to the graft by simply dip-coating the graft. Desirably, where an exterior coating only is required the lumen of the graft is protected during dipping, for example by mounting the graft onto a mandrel. The graft may simply be rotated on the surface of a gel coating solution. One or more coatings may be applied to achieve the required thickness of coating. We have found that 2, 3 or 4 coatings give good results with a dip-coating application, but 5 or more coatings may be applied, if necessary. Alternatively, the gel coating may be sprayed onto the graft.

Conveniently, the surface of the graft may be pre-wetted with a water-miscible solvent prior to application of the gel coating. Any water-miscible solvent may be suitable, but particular mention may be made of alcohols, such as ethanol and methanol, and of ketones, such as acetone.

Alternatively, the graft may be pre-treated by plasma processing.

A plasma is a partially ionised gas containing ions, electrons, atoms and neutral species, produced to create a collection of matter referred to as the $4^{th}$ state. Far any chosen procedure a suitable gas is introduced into a plasma chamber and ionised with the aid of a high frequency generator. Plasma treatments offer an unprecedented spectrum of possible surface modifications to enhance polymers, ranging from simple topographical changes to creation of surface chemistries and coatings that are radically different from the bulk polymer. Furthermore, plasma treatments are environmentally friendly and economical in their use of materials. Typically used gases include $O_2$, Ar, $N_2$ and $CF_4$, or mixtures thereof. Other suitable process gases include He, $NH_3$, $N_2O$ and $CO_2$. The plasma technique can be used to surface modify, etch, clean or activate many materials used in a multitude of applications. We have found that plasma treatment can be used to alter the surface of ePTFE in order to enhance its hydrophilic properties for subsequent coating applications. Plasma activation is the alteration of surface characteristics by the substitution or addition of new chemical groups from active species created in a plasma for groups normally present in the base polymer. Here, this process involves the replacement of highly hydrophobic ePTFE CF molecules, by highly reactive carbonyl, carboxyl and hydroxyl groups. After treatment the surface becomes temporarily reactive. It is estimated the reactive surface remains viable for up to 48 hours, although the process can be altered to create longer or shorter reactive surface properties, as required.

Plasma systems comprise 4 main components, namely a vacuum vessel, pumping group, a gas introduction and controlling system and a high frequency generator. Plasma technology is a well controlled and reproducible technique, in addition there is no substrate damage or bulk property changes except those temporarily available at the molecular level on the very outer surface of the substrate polymer. The modification that occurs to a polymeric material by exposure to a plasma is largely determined by:
1) the process gas(es),
2) the exposure time to the plasma,
3) the energy and power densities, and to a lesser degree
4) the original composition of the surface.

Types of modifications span from relatively simple surface morphological roughening or smoothing changes, to complex grafting of radically different functional groups or molecular moieties, to totally enveloping coatings that completely alter the surface properties of the bulk material. Free radical chemistry appears to be the dominant mechanistic pathway for achieving most surface modifications. In spite of the high complexity of the ensuing chemistry in a typical plasma, it is possible to tailor the process to perform specific targeted changes to polymeric surfaces (see Plasma Processing of Advanced Materials, ed. Collins and Rej, MRS Bulletin, August 1996—especially Chapter IV, Coates and Kaplan).

Highly reputible suppliers of plasma equipment intended for medical applications include Europlasma in Belgium and Hybrid Technology Services Ltd., Bristol. Both companies are heavily involved in the production of customised plasma treatment systems for numerous applications but most relevantly those in the biomedical field.

Usually only one or two layers of gel coating (for example gelatin) are required by this methodology, but occasionally 3 or more layers may be needed.

Optionally, the gel coating may be treated to induce cross-linking in the gel, for example by exposure to formaldehyde or other similar agents.

The present invention will now be further described with reference to the following, non-limiting, examples.

EXAMPLE 1

A 10% solution of gelatin in RO grade water using 1 part limed bone and 1 part succinylated gelatin was prepared daily and maintained at a constant temperature of 37° C. in an oven until used. To produce succinylated gelatin, limed bone gelatin is treated with chloride of succinic acid. Lengths of ePTFE tube were fitted securely on a mandrel. Each end of the graft was cable tied to secure the ePTFE tube for coating.

The gelatin solution was then poured into a vertical container on a hot plate. The temperature of the gelatin was maintained between 35 and 40° C. to ensure the solution did not set during use. A second vertical container with isopropanol was also prepared and the mandrel, with graft, placed into this second container for 1 minute. Excess isopropanol was removed and the mandrel was placed immediately into the gelatin solution for approximately 10 seconds. The isopropanol bath prepares the exterior, hydrophobic surface of the ePTFE material to receive the gelatin by wetting the exterior surface. The mandrel was manually rotated in the gelatin solution to ensure complete coverage of the ePTFE tube. On removal the gelatin was manually massaged along the length of the tube while being rotated in front of a cold air fan. This procedure was performed immediately upon removal of the ePTFE graft from the gelatin solution. Massage was stopped as soon as the gelatin began to feel tacky. Excess manual action led to non-uniformity and peeling of the coating. The mandrel, with graft, was left in front of a cold blowing fan to dry completely before applying a second coating. After application of a final third coating, the graft was left to dry for 1 hour until hard. After drying, the graft was detached from the cable ties and the coated graft removed from the mandrel. A third vertical container with 50% solution of formaldehyde was also prepared and the coated graft placed in this solution overnight to induce cross-linking.

The coated PTFE graft was removed after cross-linking and washed for a minimum of 5 hours before being plasticised. For this process an 80% glycerol solution was prepared and heated to 65° C. in a water bath. Coated grafts were placed in this solution for 30 minutes until they felt soft and flexible. The grafts were removed from the glycerol solution for a final wash. Final washing involved submersion for 15 minutes in isopropanol at 125 rpm to remove excess glycerol. The treated grafts were finally air dried with a fan. Before final sterilisation and packaging, coated ePTFE grafts were gently extended manually from their coated compressed state to aid flexibility and extendibility.

EXAMPLE 2

A 15% solution of gelatin in RO grade water was prepared daily and maintained at a constant temperature of 37° C. in an oven until used. Lengths of ePTFE tube were fitted securely on a mandrel. Each end of the graft was cable tied to secure the ePTFE tube for coating.

The gelatin solution was then poured into a vertical container on a hot plate. The temperature of the gelatin solution was maintained between 35 and 40° C. to ensure the solution did not set during use. A second vertical container with isopropanol was also prepared and the mandrel, with graft, was placed into this second container for 1 minute. Excess isopropanol was removed and the mandrel was placed immediately into the gelatin solution for approximately 15 seconds. During this time the mandrel was manually rotated to ensure complete coverage of the ePTFE tube. On removal the gelatin was manually massaged along the length of the tube while being rotated in front of a cold air fan. This procedure was performed immediately upon removal of the ePTFE graft from the gelatin solution. Massage was stopped as soon as the gelatin began to feel tacky. Excess manual action led to non-uniformity and peeling of the coating. The mandrel, with graft, was left in front of a cold blowing fan to dry completely before applying a second coating. After application of a final third coating, the graft was left to dry for 1 hour until hard. After drying, the graft as detached from the cable ties and the coated graft was removed from the mandrel. A third vertical container containing a 50% solution of formaldehyde was also prepared and the coated graft placed in this solution overnight to induce cross-linking.

The coated PTFE graft was removed after cross-linking and washed for a minimum of 5 hours before being plasticised. For this process an 80% glycerol solution was prepared and heated to 70° C. in a water bath. Coated grafts were placed in this solution for 30 minutes until they felt soft and flexible. The grafts were removed from the glycerol solution for final wash. Final washing involved submersion for 15 minutes in isopropanol at 125 rpm to remove excess glycerol. PTFE grafts were finally air dried with a fan. Before final sterilisation and packaging, coated ePTFE grafts were gently extended manually from their coated compressed state to aid flexibility and extendibility.

Expanded polytetrafluoroethylene vascular grafts treated according to the described techniques display an unexpectedly increased longitudinal extensibility over uncoated grafts. Longitudinal extensibility is desirable for reducing the need for precise length adjustment during implantation. In general, past treatments to increase the stretchableness of ePTFE grafts have employed thermal treatments which modify the node/fibril structure of the grafts. The grafts according to the present invention provide increased longitudinal extensibility without altering the node/fibril structure of the graft.

The improved characteristics of the graft were tested using an elongation test. In this test, the lengths of uncoated and coated vascular grafts were measured. One end of the grafts was secured and selected weights were suspended from the opposite end. The elongated length was measured and the percent increase in length was calculated. The weights were removed from the coated grafts and the grafts were allowed to return to an unloaded length after elongation. The unloaded length after elongation was measured and the selected weights were re-applied. A second elongated length was measured and the percent increase of the second elongated length over the unloaded length after elongation was calculated. The results observed are recorded in the following Table 1.

TABLE 1

| Weights applied (g) | Percent increase in length | | |
|---|---|---|---|
| | Uncoated | Coated | Coated, after elongation |
| 125 | 2 | 13 | 7 |
| 250 | 4 | 16 | 15 |
| 500 | 4 | 24 | 20 |
| 1000 | 4 | 28 | 27 |

From the foregoing description it should be apparent that the present invention provides an ePTFE vascular graft with a substantially uniform coating of a bioresorbable gel on an outer surface. Further it will be apparent that various changes may be made in the form of the elements thereof without departing from the spirit and scope of the invention, the form and examples hereinbefore described being merely exemplary embodiments.

EXAMPLE 3

Coated PTFE In-Vitro Testing

Coated ePTFE grafts prepared according to Example 1 and equivalent uncoated ePTFE grafts were pressurised with citrated animal blood at 120 mm of mercury. A 5/0 prolene suture was then passed through the graft. Blood loss was measured and the graft photographed. The method was repeated using the normal leak testing mixture of propanol and glycerol.

Figure 4:
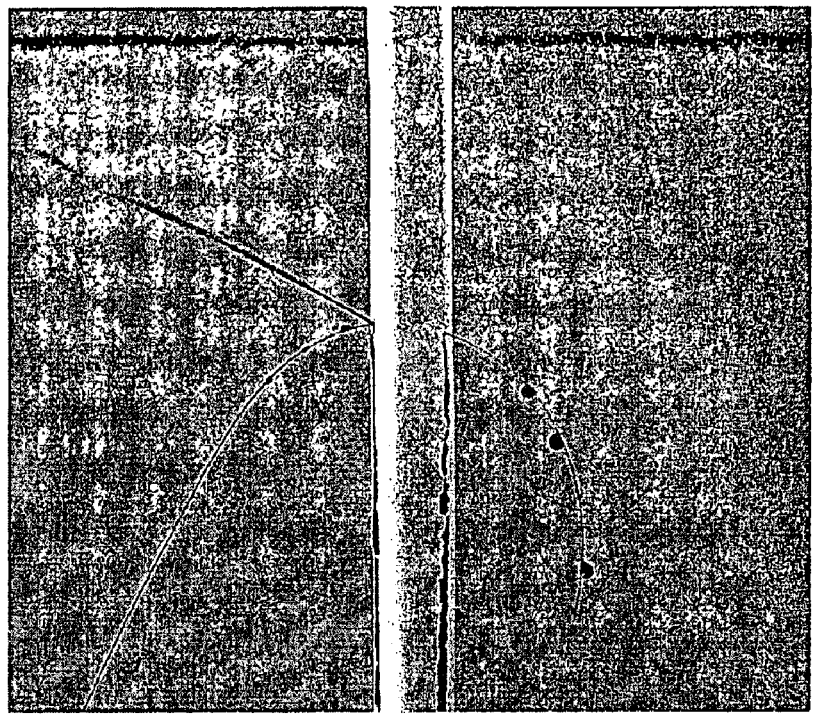
FIG. 4 is a photograph of a prior art uncoated ePTFE graft showing the suture hole leakage due to 5/0 prolene suture.
Figure 5:
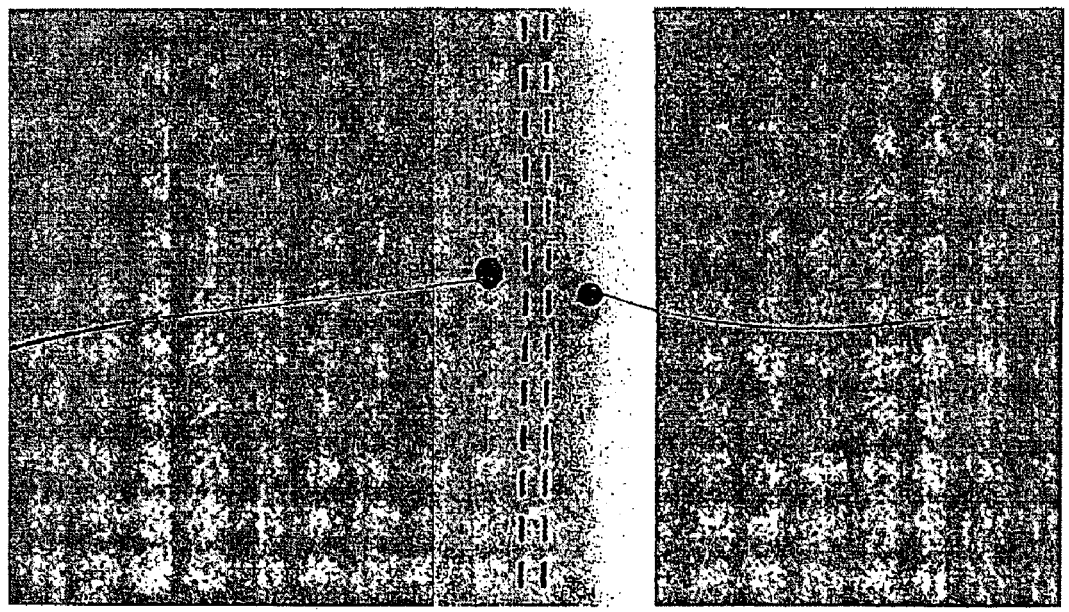
FIG. 5 is a photograph of a coated ePTFE graft according to the invention showing the suture hole leakage due to a 5/0 prolene suture.

The results are in Table 2 and the photographs are FIGS. 4 and 5.

It is clear that the gelatine coating present on the coated PTFE grafts according to the present invention provides a dramatic reduction in suture hole bleeding.

Figure 6:
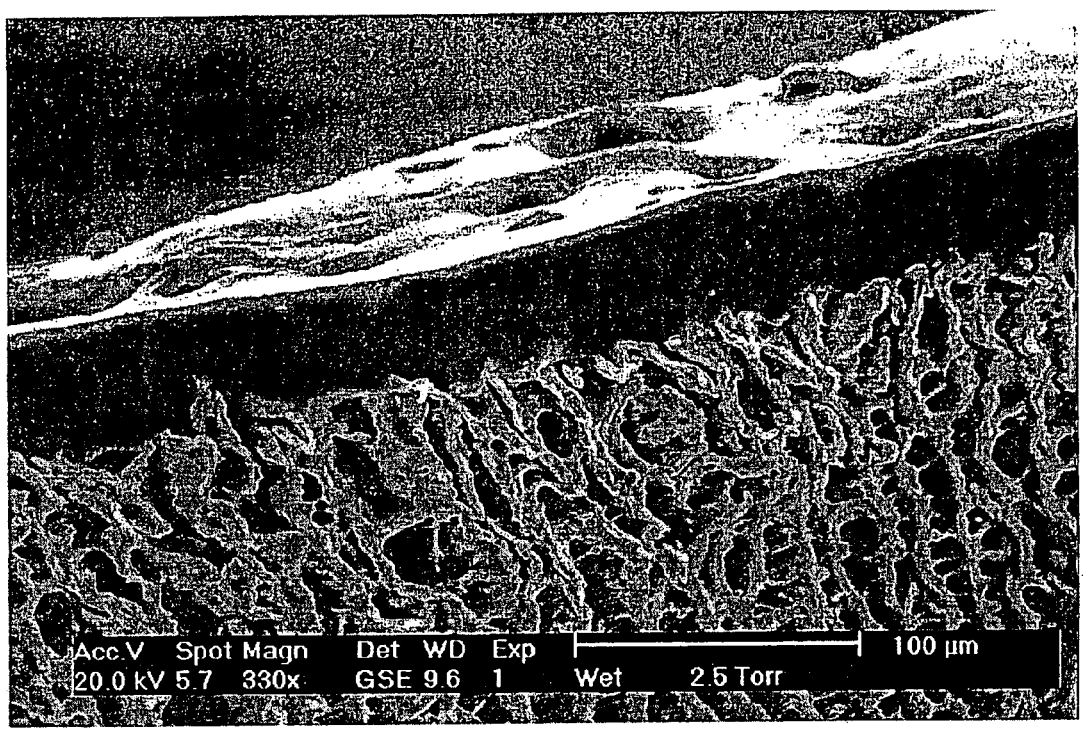
FIG. 6 is a photomicrograph showing a coated ePTFE graft according to the invention (magnification ×330).

Environmental scanning electron microscopy (variable pressure SEM) was used to visualise the gelatin coating in its hydrated state. The image in FIG. 6 shows a uniform layer around 50 $\mu$m thick which penetrates a short distance of less than 50 $\mu$m, preferably less than 20 $\mu$m, for example less than 10 $\mu$m, into the surface of the ePTFE.

The usual physical parameters were measured before and after coating the graft. No reduction in any parameter was noted. As an example, the figures for suture retention are given in Table 3. A slight increase is noted after coating.

TABLE 2

Suture hole leakage rates of coated ePTFE vs uncoated ePTFE

| Sample | Blood leakage (ml/minute) | Leakage rate (ml/cm$^2$/min) |
| --- | --- | --- |
| Thin wall coated ePTFE | <5 | 7.1 |
| Thin wall uncoated ePTFE | >40 | 11.3 |
| Standard wall coated ePTFE | <5 | 7.5 |
| Standard wall uncoated ePTFE | >40 | 13.9 |

TABLE 3

Suture retention results of coated ePTFE and uncoated ePTFE

|  | Suture retention (Newtons) |
| --- | --- |
| coated ePTFE | 8.5 |
| uncoated ePTFE | 7.51 |

EXAMPLE 4

Animal Testing

Standard ePTFE (Sulzer Vascutek) and coated ePTFE grafts prepared according to Example 1 were evaluated by comparison with conventional ePTFE grafts (obtained from Impra) in an infra renal canine model.

The gelatin sealed ePTFE graft demonstrated good handling and suturing characteristics, as well as impressive acute hemostatic properties in terms of blood loss and time of hemostasis, as compared to both the Sulzer Vascutek and Impra conventional (unsealed) ePTFE grafts.

The efficacy of gelatin impregnated ePTFE grafts in a canine abdominal model, both in terms of the role of the gelatin in preventing blood loss and oozing near the anastomoses at the time of surgery and in maintaining acute graft hemostasis, was assessed.

Materials and Methods
Graft Selection

A gelatin ePTFE vascular graft, 6 mm in diameter, was used. The structure is made of solid nodes of PTFE interconnected by numerous thin microfibrils of PTFE. The fibrils are oriented along the longitudinal axis of the graft, namely, in the direction of blood flow, while the nodes are perpendicular to this same axis. The thin wall ePTFE graft was impregnated with gelatin according to Example 1.

Animal Selection

Seven adult mongrel dogs of either sex, each weighing between 20 and 25 kg, were selected and treated according to the Canadian Council on Animal Care regulations. Prior to surgery, routine hematological tests were performed, including hematocrit, leukocyte and platelet counts, platelet aggregation and thromboelastography.

Surgery

The dogs were fasted for 24 hours prior to surgery. They were administered an I.M. premedication bolus of 0.05 mg/kg of atropine sulfate (MTC Pharmaceuticals, Cambridge, ON, Canada) and 0.1 mg/kg of acepromazine maleate (Atravet®, Ayerst Laboratories, Montreal, QC, Canada). They were then anesthesized with 10 mg/kg I.V. of sodium thiopental (Pentothal®, Abbott Laboratoires, Montreal, QC, Canada), intubated and mechanically ventilated. Isoflurane gas (Aerrane®, Janssen, North York, ON, Canada) was used to maintain anesthesia as required. Intravenous infusions of Ringer's lactate was injected to compensate for dehydration during surgery. The abdomen was shaved and the skin disinfected with Hibitane® chlorhexidrine gluconate (Ayerst) and 10% Proviodine® iodine USP topical solution (Rougier, Chambly, QC, Canada).

A midline lower abdominal incursion was performed and the abdominal aorta was isolated from the renal arteries to the aortic trifurcation. After collateral ligation, the animals were given 0.5 mg/kg of intravenous heparin (Hepalean®, Organon Teknika Inc, Toronto, ON, Canada) at least 5 minutes prior to vascular clamping. The gelatin ePTFE grafts were 6 mm in diameter and 5 cm in length. Each end-to-end anastomosis was performed with 6/0 Surgilene® polypropylene monofilament sutures (CF-30) with double-armed, atraumatic taper needles (Davis & Geck, Newark, N.J., USA). Following the release of the clamps, the blood loss through the needle holes was measured under a strict protocol described in the following section. Upon complete hemostasis, the abdomen was closed in layers using 2/0 Vicryl® and PDS monofilament sutures, and the skin was stapled. Upon awakening, the animals were returned to their cages and fed an unrestricted standard diet. They also received 0.2 mg/kg of butorphanol tartrate (Torbugesic®, Ayerst) for 3 days as a post-operative analgesic.

Acute Hemostasis

In order to assess the bleeding through the needle holes after completion of both end-to-end anastomoses of the gelatin ePTFE graft, a protocol was designed to measure the blood loss immediately following the release of the vascular clamps. This was determined by counting blood-soaked medical gauzes as well as the volume of blood, if any, removed by suction. Laboratory tests have shown that approximately 15 ml of blood may be retrieved in one medical gauze. By counting the number of blood-soaked gauzes and the volume obtained by suction, it was possible to approximate the blood loss from each graft. The protocol included a series of steps designed to reduce post-operative blood loss. Phase 1 was the first 10-minute period after the release of the clamps where blood was collected freely; Phase 2 was the time interval between 10 and 20 minutes where a piece of cellulose wrapping (Surgicel™, Johnson & Johnson Medical Inc, Arlington, Tex., USA) was placed around the anastomotic lines to help stop blood leakage; and Phase 3 covered the period after 20 minutes of blood loss, where the heparin effect was reversed by half a dose of protamine sulfate (Fujisawa Canada Inc, Markham, ON, Canada). Hemostasis was usually achieved approximately 30 to 40 minutes after the release of the clamps. The amount of blood loss and time of complete hemostasis were then recorded by a trial coordinator after deliberation with, but independent of, the surgeon.

Statistical Analysis

The results regarding blood loss and the time of complete hemostasis were compared for statistical significance using an ANOVA analysis where a p value of <0.05 was considered statistically significant.

Results

Implantation and Follow-up

All 7 operations were successful with no mortality or morbidity reported. The handling and suturing characteristics of the gelatin ePTFE grafts were satisfactory. The mean time required to perform the two end-to-end anastomoses was 23.0±5.8 min and compared favourably with those of a standard (uncoated) thin wall ePTFE graft from Sulzer Vascutek (23.3±4.6 min) and from Impra (23.4±3.5 min) which were recorded in a previous study.

Acute Hemostasis

Figure 7:
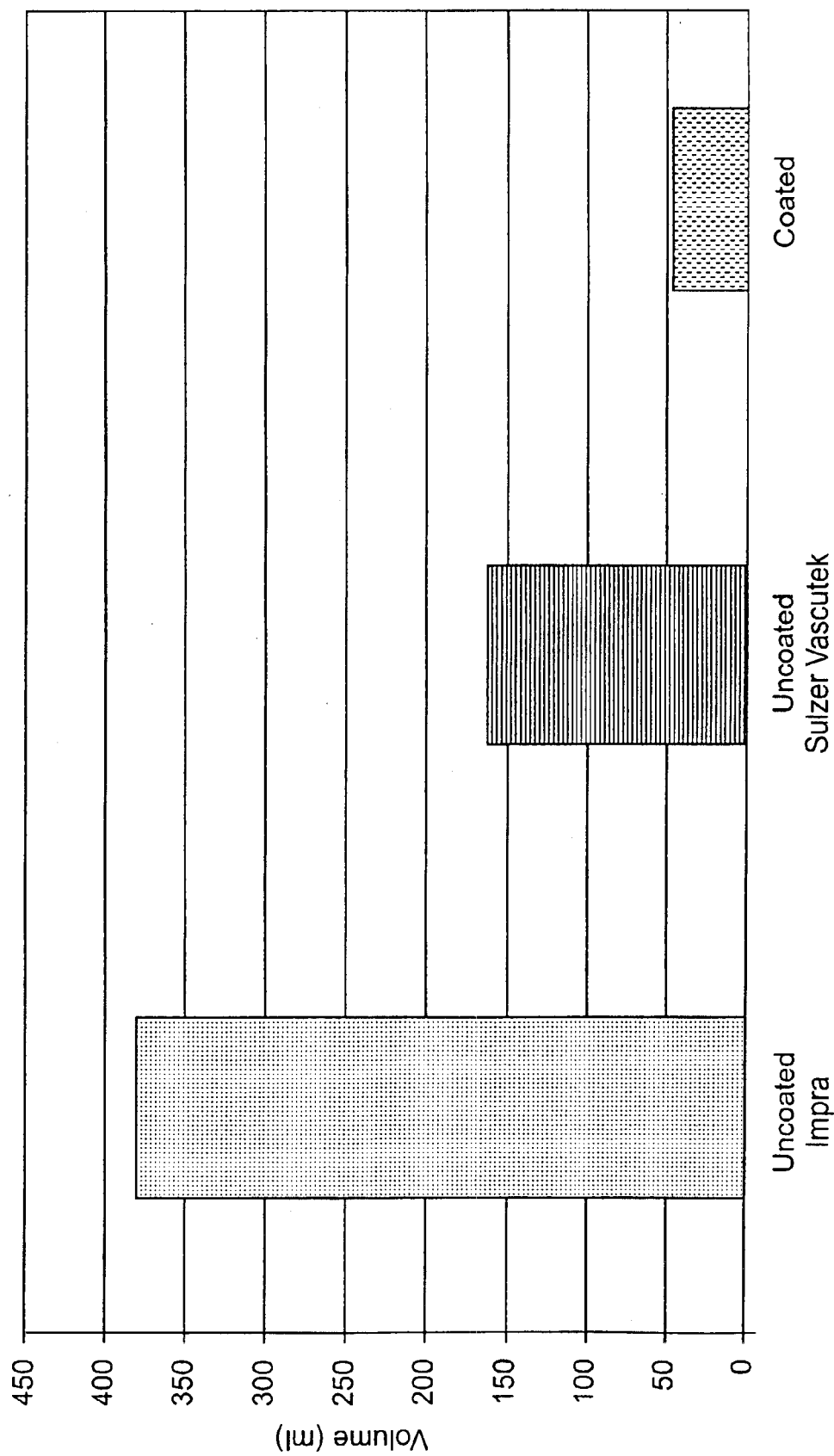
FIG. 7 is a graph summarising the blood loss from different ePTFE grafts post implantation in Example 5.
Figure 8:
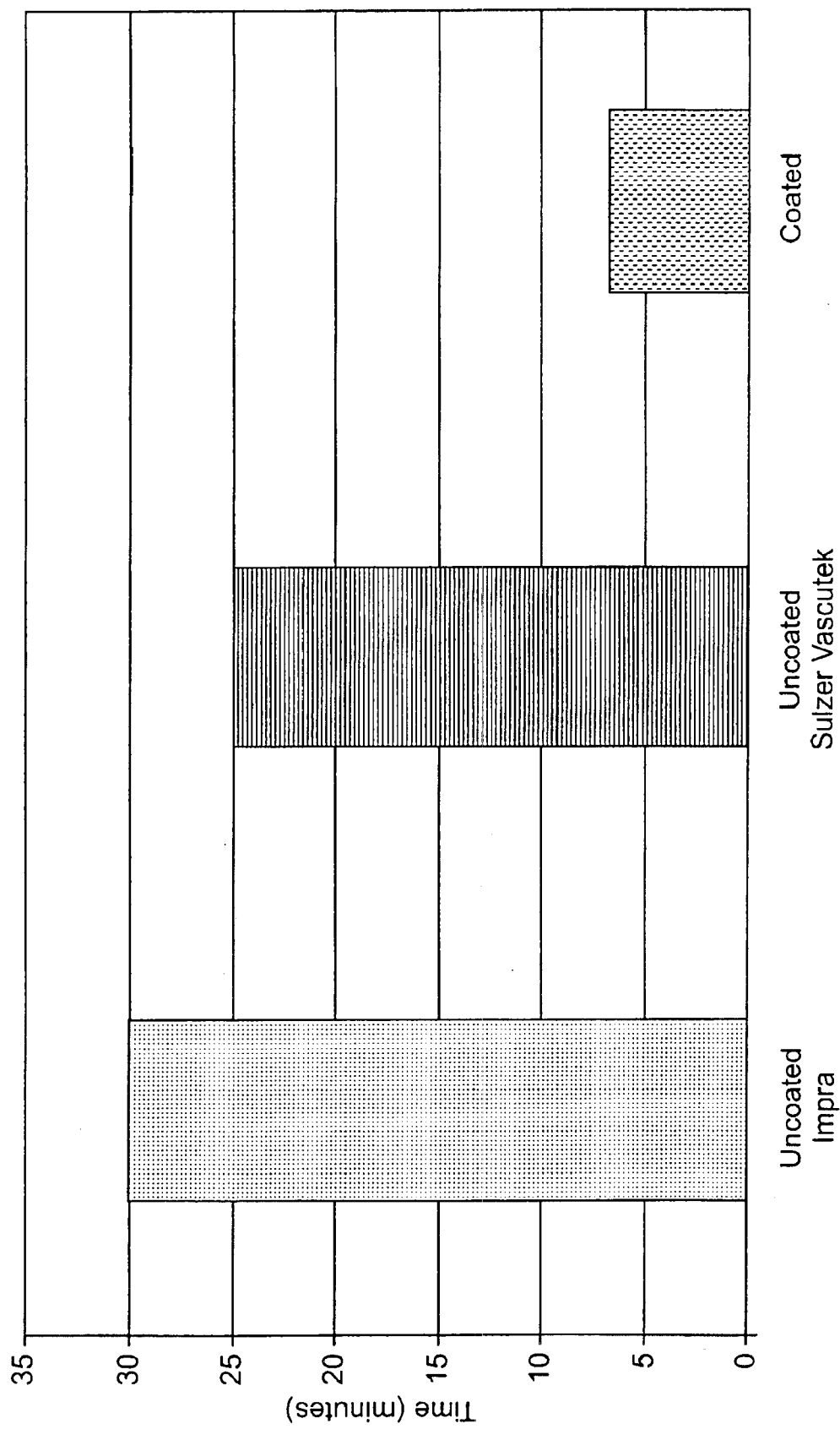
FIG. 8 is a graph showing the time taken to reach haemostasis of different ePTFE grafts post implantation in Example 5.
Figure 9:
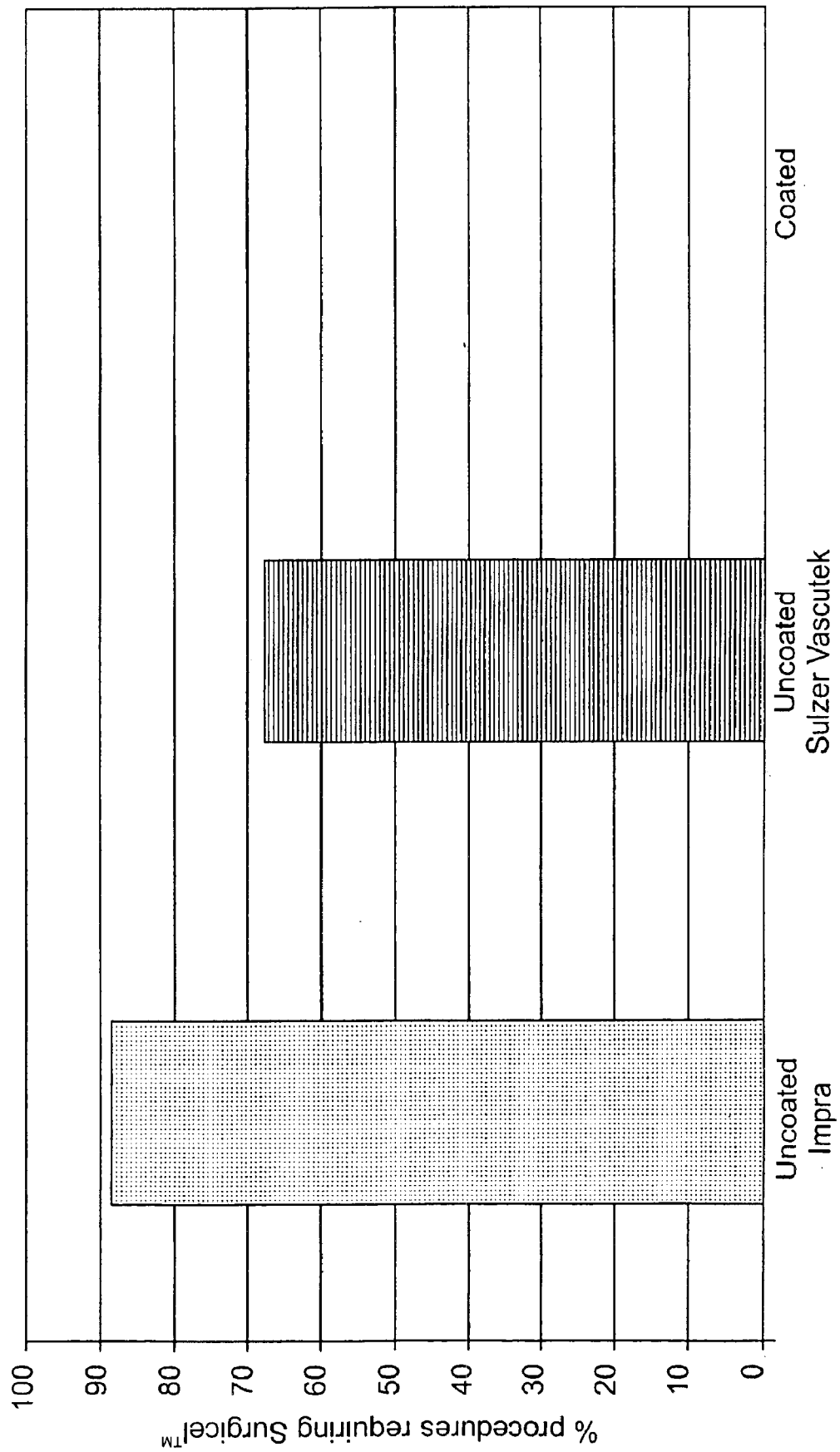
FIG. 9 is a graph showing the percentage of surgical procedures in Example 5 involving different ePTFE grafts requiring SURGICEL™ application to control blood loss.

Table 4 presents the blood loss through the anastomotic lines and the time of complete hemostasis observed with the gelatin ePTFE graft. The blood loss measured for the gelatin ePTFE grafts was 44.0±21.6 ml and found to be significantly less than those of both the (uncoated) thin wall ePTFE grafts from Sulzer Vascutek (161.4±54.3 ml) and from Impra (380.6±245.6 ml)(p<0.05). The results are presented in FIG. 7. Similarly, the time of complete hemostasis was also less for the gelatin ePTFE graft (6.6±3.0 min) compared to the control standard thin wall (uncoated) ePTFE graft from Sulzer Vascutek (20.2±9.9 min) and from Impra (30.1±10.7 min) (measured in a previous study)(see FIG. 8). In addition, under the designed protocol, the use of the cellulose wrapping (see FIG. 9) and the protamine sulfate (see FIG. 10) after 10 and 20 min of bleeding, respectively, were not necessary with the gelatin ePTFE grafts.

CONCLUSION

The gelatin ePTFE graft demonstrated good handling and suturing characteristics as well as impressive acute hemostatic properties in terms of blood loss and time of hemostasis as compared to the uncoated control grafts.

TABLE 4

Blood loss and hemostasis for ePTFE grafts

| Prosthesis | Blood loss (ml) | Hemostasis (min) | Surgicel ™ | Protamine |
|---|---|---|---|---|
| Uncoated (Impra) | 380.6 ± 254.6 | 30.1 ± 10.7 | 8/9 | 6/9 |
| Uncoated (Sulzer Vascutek) | 161.4 ± 54.3 | 20.2 ± 9.9 | 6/9 | 3/9 |
| Coated ePTFE | 44.0 ± 26.6 | 6.6 ± 3.0 | 0/5 | 0/5 |

EXAMPLE 5

Surface coating of ePTFE vascular grafts following radio frequency plasma modification We have successfully coated ePTFE grafts using an optimised $O_2$ plasma system fed with 1000 W, 40 kHz rf power with oxygen flow 20 sccm (standard cubic centimeters per minute), between 0.5 and 1 torr. Suitable plasma equipment can be obtained from Europlasma, Belgium, or Hybrid Technology Services, Bristol, UK. Treatment time was approximately 30 minutes although both longer and shorter exposure times have proved equally successful. Immediately after plasma exposure or within a 48 hour time period an ePTFE vascular graft substrate was successfully dip coated with gelatin without the need of additional surface modification processes e.g. alcohol pre-soak. The further application of only one additional layer provided a sealed ePTFE vascular graft equivalent to those currently coated manually by 4 layers of gelatin sealant. Cross-linking, washing and plasticisation steps may be included as described in Examples 1 and 2. No changes in the sealant properties or physical properties of the ePTFE substrate were observed under scrutiny by Scanning Electron Microscopy. Successful dip coating was also achieved using a combination of other gases such as Nitrogen/Hydrogen mixes and Argon.

What is claimed is:

1. A method of preparing an implantable vascular graft comprising:
   a) preparing an expanded polytetrafluoroethylene substrate having a wall structure with an inside wall and an outside wall,
   b) preparing a solution of gel,
   c) covering at least one wall of said substrate with a coating of said gel, and cross-linking said coating, wherein said covering step comprises plasma treatment of said substrate.

2. The method of claim 1 wherein said covering step comprises immersing said graft in a water-miscible solvent to pre-wet the substrate.

3. The method of claim 2 wherein said water-miscible solvent is isopropanol.

4. The method of claim 1, wherein said plasma treatment uses oxygen, argon, nitrogen, tetrafluorocarbon gas or mixtures thereof as a process gas.

5. The method of claim 1, wherein said covering step comprises rotating said substrate in a container of gel solution.

6. The method of claim 1 wherein said covering step further comprises massaging said gel in an air stream.

7. The method of claim 1 further comprising the steps of plasticising said gel with glycerol, and drying said implantable vascular graft.

8. The method of claim 1 further comprising washing said graft for at least about 5 hours.

9. The method of claim 7 wherein said glycerol solution is an 80% glycerol solution.

10. An implantable vascular graft constructed according to the method of claim 1.

11. A method of vascular anastomosis comprising attaching a vascular graft according to claim 10 to a blood vessel of a patient.

12. The method of claim 11 wherein said vascular graft is attached to said blood vessel by suture.

* * * * *